US011730452B2

(12) United States Patent
Levy

(10) Patent No.: US 11,730,452 B2
(45) Date of Patent: Aug. 22, 2023

(54) SYSTEMS AND METHODS FOR REGULATING MICROBUBBLES IN ULTRASOUND PROCEDURES

(71) Applicant: Yoav Levy, Hinanit (IL)

(72) Inventor: Yoav Levy, Hinanit (IL)

(73) Assignee: INSIGHTEC LTD., Tirat Carmel (IL)

( * ) Notice: Subject to any disclaimer, the term of this patent is extended or adjusted under 35 U.S.C. 154(b) by 758 days.

(21) Appl. No.: 16/378,945

(22) Filed: Apr. 9, 2019

(65) Prior Publication Data

US 2020/0323515 A1 Oct. 15, 2020

(51) Int. Cl.
| | |
|---|---|
| *A61B 8/08* | (2006.01) |
| *A61N 7/02* | (2006.01) |
| *G01S 15/89* | (2006.01) |
| *A61N 7/00* | (2006.01) |

(52) U.S. Cl.
CPC .............. *A61B 8/481* (2013.01); *A61N 7/02* (2013.01); *G01S 15/895* (2013.01); *A61N 2007/0039* (2013.01)

(58) Field of Classification Search
CPC ... A61B 8/481; A61B 6/032; A61B 2034/107; A61B 2034/105; A61B 2090/374; A61B 6/488; A61B 6/03; A61B 34/10; A61B 8/54; A61B 8/5292; A61B 8/4488; A61B 8/4416; A61B 8/085; A61B 8/0808; A61N 7/02; A61N 2007/0039; A61N 2007/0095; A61N 2007/0021; A61N 7/00; G01S 15/895; G01R 33/4814; A61M 37/0092
See application file for complete search history.

(56) References Cited

U.S. PATENT DOCUMENTS

| | | | |
|---|---|---|---|
| 7,278,968 B2 | 10/2007 | Umemura et al. | |
| 8,016,757 B2 * | 9/2011 | Kaczkowski | ......... A61B 5/015 600/438 |
| 9,743,909 B1 * | 8/2017 | Sapozhnikov | ........... A61N 7/02 |

(Continued)

FOREIGN PATENT DOCUMENTS

| | | | | |
|---|---|---|---|---|
| EP | 3421090 A1 | 1/2019 | | |
| WO | WO-2014135987 A2 * | 9/2014 | ............... | A61N 7/00 |

(Continued)

OTHER PUBLICATIONS

Insightec, Ltd., International Search Report and Written Opinion, PCTIB2020000256, dated Jul. 13, 2020, 11 pgs.

*Primary Examiner* — Boniface Ngathi N
*Assistant Examiner* — Zainab Mohammed Aldarraji
(74) *Attorney, Agent, or Firm* — Morgan, Lewis & Bockius LLP

(57) ABSTRACT

Various approaches for regulating microbubbles in a treatment procedure for a target include generating a tissue-sensitivity map including multiple regions, at least one of the regions being outside the target region, the tissue-sensitivity map assigning, to each of the regions, a sensitivity level indicative of tissue sensitivity to the interaction between the microbubbles and an acoustic beam; select one or more interaction regions based at least in part on the tissue-sensitivity map; and activating the ultrasound transducer so as to generate the acoustic beam for interacting with the microbubbles in the selection interaction region(s) in the tissue-sensitivity map, thereby indirectly changing a characteristic of the microbubbles at the target region.

32 Claims, 11 Drawing Sheets

(56) References Cited

U.S. PATENT DOCUMENTS

| | | | |
|---|---|---|---|
| 10,575,816 B2 * | 3/2020 | Prus | A61B 8/4494 |
| 10,765,892 B1 * | 9/2020 | Vitek | A61B 34/10 |
| 2007/0016039 A1 * | 1/2007 | Vortman | A61N 7/02 600/439 |
| 2012/0029396 A1 * | 2/2012 | Vortman | A61N 7/02 601/2 |
| 2015/0196638 A1 * | 7/2015 | Czarnota | A61N 7/00 600/1 |
| 2015/0359603 A1 * | 12/2015 | Levy | A61N 7/02 703/2 |
| 2015/0360020 A1 | 12/2015 | Wu et al. | |
| 2017/0358095 A1 * | 12/2017 | Levy | G01R 33/56308 |
| 2018/0071553 A1 * | 3/2018 | Vortman | A61N 7/022 |
| 2019/0009109 A1 * | 1/2019 | Vortman | A61N 7/00 |

FOREIGN PATENT DOCUMENTS

| | | | | |
|---|---|---|---|---|
| WO | WO-2015200576 A1 * | 12/2015 | | A61K 47/6913 |
| WO | WO2018138576 A1 | 8/2018 | | |
| WO | WO2019002940 A1 | 1/2019 | | |

\* cited by examiner

SYSTEMS AND METHODS FOR REGULATING MICROBUBBLES IN ULTRASOUND PROCEDURES

FIELD OF THE INVENTION

The present invention relates, generally, to ultrasound procedures, and more particularly to systems and methods for regulating microbubbles during such procedures for increasing the efficiency thereof while avoiding damage to healthy tissue.

BACKGROUND

Focused ultrasound (i.e., acoustic waves having a frequency greater than about 20 kiloHertz) can be used to image or therapeutically treat internal body tissues within a patient. For example, ultrasound waves may be used in applications involving ablation of tumors, targeted drug delivery, disruption of the blood-brain barrier (BBB), lysing of clots, and other surgical procedures. During tumor ablation, a piezoceramic transducer is placed externally to the patient, but in close proximity to the tumor to be ablated (i.e., the target region). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer. Magnetic resonance imaging (MRI) may be used to visualize the patient and target, and thereby to guide the ultrasound beam.

During a focused ultrasound procedure, small gas bubbles (or "microbubbles") may be generated and/or introduced into the target region. Because the microbubbles encapsulate gas, the bubble surfaces may collectively form an ultrasound reflector. Thus, by transmitting the ultrasound waves to the microbubbles and receiving reflections therefrom, the amplitudes and/or phases associated with the reflected ultrasound can be determined; based thereon, the transducer parameters (e.g., phase shifts and/or amplitudes) can be determined or adjusted to compensate for the aberrations caused at least in part by the skull. While this approach may effectively improve the focusing properties at the target, the microbubbles left in the target and/or non-target tissue after the focusing procedure may cause undesired damage. For example, the reaction of tissue containing a higher relative percentage of microbubbles during the subsequent application of the ultrasound energy for target treatment is non-linear and difficult to predict. In addition, depending upon the amplitude and frequency of the applied acoustic field, the microbubbles may oscillate or collapse (a phenomenon known as "cavitation") and thereby cause extensive tissue damage beyond that targeted, and may be difficult to control. As used herein, the response of microbubbles to the applied sonication is referred to as the "microbubble response," and the thermal or mechanical effect (e.g., tissue rupture due to mechanical stress caused by collapsing microbubbles) in the target and/or non-target regions resulting from the sonication and/or microbubble cavitation is referred to as the "therapeutic effect."

To minimize the unwanted effects resulting from the microbubbles during treatment of the target, one conventional approach suspends the ultrasound procedure until the microbubbles have dissipated naturally. This approach, however, unnecessarily and undesirably extends the duration of the ultrasound procedure. Another conventional approach for eliminating microbubbles applies low-energy sonications to cause the microbubbles to undergo cavitation. This approach may cause rather than avoid cavitation-induced damage to non-target tissue, however. Accordingly, there is a need for approaches that efficiently clear microbubbles during an ultrasound procedure so as to avoid damage to healthy tissue.

SUMMARY

The present invention relates to regulation of an amount or a concentration of microbubbles prior to and/or during a target treatment procedure (e.g., an ultrasound procedure) in a manner that retains the efficiency of the ultrasound procedure while avoiding damage to healthy, non-target tissue. In various embodiments, the microbubble-regulating approach involves creation of a tissue-sensitivity map of one or more tissue regions outside the target region prior to the treatment procedure. In one implementation, the target region and/or the regions outside the target are represented as three-dimensional (3D) sets of voxels (i.e., volumetric pixels), and each voxel is associated with a sensitivity score indicating tissue sensitivity to the interaction between the applied sonications and microbubbles. For example, the tissue sensitivity may be thermal sensitivity and/or sensitivity to microbubble cavitation. A relatively high sensitivity score indicates that the tissue corresponding to the voxel may be more sensitive to (e.g., tolerate a relatively low) temperature increase and/or microbubble cavitation events and is therefore more easily damaged; whereas a relatively low sensitivity score indicates that the tissue is less sensitive (e.g., having a relatively large tolerance) to the temperature increase and/or microbubble cavitation.

In some embodiments, prior to and/or during the ultrasound procedure (e.g., applying sonications to ablate the target tissue), a small cloud of transient microbubbles is provided to the target region for autofocusing acoustic beams applied thereon. After the transducer parameters (e.g., frequencies, phase shifts and/or amplitudes) that optimize the focus at the target region are determined (e.g., via analysis of the acoustic reflections from the microbubbles), the tissue-sensitivity map may be utilized to eliminate (or at least reduce) the microbubbles at the target region and/or its nearby region so as to avoid undesired damage resulting therefrom. The presence and/or the amount (or concentration) of microbubbles at the target region (and/or its nearby non-target region) is measured based on acoustic signals transmitted or reflected from the microbubbles using an acoustic-signal detection device and/or a transducer array. If the microbubbles are present and/or the amount or concentration thereof exceeds a predetermined threshold, the measures described below may be taken. The threshold may be set based on, for example, a previously performed ultrasound procedure that was effective without damaging non-target tissue, in which case the affected non-target tissue zone may be considered tolerant at least to this level of microbubbles. Alternatively, microbubble thresholds can be estimated based on a known relationship (which may be approximate) among tissue temperature sensitivities (or tolerances) and the effect of microbubble cavitation (at a given applied power and microbubble concentration) on the tissue in question.

In various embodiments, based on the tissue-sensitivity map, one or more regions that are relatively less sensitive (e.g., having lower sensitivity scores) to the interaction of the acoustic beam and microbubbles in the tissue-sensitivity map can be identified. The ultrasound transducer may then be activated to generate one or more foci at the identified region(s) so as to clear the microbubbles (e.g., by causing cavitation thereof) therein. Optionally, the microbubble cavitation may be monitored in real time using, again, the acoustic-signal detection device and/or transducer array. Based thereon, the ultrasound parameters may be adjusted to ensure that a desired proportion of microbubbles are destroyed without damaging tissue even in the relatively low sensitivity region(s). Because this approach may reduce the overall amount of microbubbles in the bloodstream, the amount of microbubbles in the target region (as well as everywhere in the bloodstream) can be indirectly reduced. As a result, the undesired damage resulting from the microbubbles at the target and/or its nearby non-target regions during ablation of the target tissue may be avoided. In addition, because the microbubbles are destroyed in the region(s) having relatively low sensitivities to the temperature increase and/or microbubble cavitation, damage to the low-sensitivity region(s) may be clinically insignificant. As used herein, "clinically insignificant" means having an undesired (and sometimes the lack of a desired) effect on tissue that is considered insignificant by clinicians, e.g., prior to the onset of damage thereto or other clinically adverse effect, whether temporary or permanent. In addition, "indirect" reduction of microbubbles in a region means that the ultrasound focus is not directed to and/or generated in such a region that may directly cause microbubble cavitation to occur therein.

In some embodiments, the amount of microbubbles present in the regions on the tissue-sensitivity map may be taken into account when determining the region(s) in which the microbubbles are to be cleared. For example, applying the acoustic beam to a region having a relatively large amount of microbubbles may result in more microbubble cavitation, and thereby more efficiently reduces the microbubble population in the target region (and everywhere in the blood stream). The amount of microbubbles in various regions may be detected using the acoustic reflections from the microbubbles as described above. Additionally or alternatively, the region(s) in which the microbubbles are to be cleared may be selected based on a relative location of the region(s) with respect to the target region. For example, destroying microbubbles in a region that is upstream of the target region may promptly reduce the microbubble population in the target; whereas destroying microbubbles in a region that is downstream of the target region may reduce the microbubble population in the target, but the effect at the target may be delayed because of the longer circulation path back to the target.

While the main force for distributing microbubbles in the target region and regions outside the target is blood circulation, in some embodiments, the ultrasound transducer may be configured (e.g., by adjusting the phases, amplitudes and/or frequencies) to create a focus that can induce movement of microbubbles by applying an acoustic force thereto. The ultrasound parameters (e.g., phases) may be adjusted so as to gradually move the focus (and thereby the microbubbles) from the vulnerable region (e.g., the target and/or a relatively high-sensitivity region) toward the identified relatively low-sensitivity region. Once the microbubbles have been moved from the vulnerable tissue into a region of lower sensitivity, the intensity of the acoustic beams may be increased to cause microbubble cavitation in order to clear the microbubbles. Again, the microbubble movement and/or cavitation may be monitored in real time using the acoustic-signal detection device and/or transducer array. Based thereon, the ultrasound parameters may be adjusted to ensure that a desired portion of microbubbles are moved away from the relatively high-sensitivity region(s) without cavitation as well as the absence of cavitation that might cause damage even in the relatively low-sensitivity region(s).

After the microbubbles are eliminated/reduced, the ultrasound procedure for treating the target tissue may start or continue. Accordingly, various embodiments utilize a tissue-sensitivity map to identify one or more regions that have lower sensitivity (or higher tolerance) to the acoustic power and/or microbubble cavitation, and based thereon, configure the ultrasound transducer to cause cavitation of microbubbles in the identified lower-sensitivity region(s). This may advantageously avoid undesired damage to the healthy tissue resulting from cavitation of microbubbles while obviating the need to prolong the ultrasound procedure as required in conventional approaches that pause until the microbubbles have cleared naturally.

Accordingly, in one aspect, the invention pertains to a system for regulating microbubbles in a treatment procedure for a target region. In various embodiments, the system includes an ultrasound transducer and a controller configured to (a) generate a tissue-sensitivity map including multiple regions, one or more of the regions being outside the target region; (b) select one or more interaction regions based at least in part on the tissue-sensitivity map; and (c) activate the ultrasound transducer so as to generate an acoustic beam for interacting with microbubbles in the selected interaction region(s) in the tissue-sensitivity map, thereby indirectly changing a characteristic of the microbubbles (e.g., the amount, concentration, size distribution and/or response of the microbubbles to the acoustic beam) at the target region. In one implementation, the tissue-sensitivity map assigns, to each region in the tissue-sensitivity map, a sensitivity level indicative of tissue sensitivity (e.g., thermal sensitivity and/or sensitivity to microbubble cavitation) to an interaction between the microbubbles and the acoustic beam.

The controller may be further configured to determine one or more parameters (e.g., a frequency, an amplitude and/or a phase) associated with one or more transducer elements of the ultrasound transducer based at least in part on the selected interaction region(s) in the tissue-sensitivity map. In addition, the controller may be further configured to activate the ultrasound transducer based at least in part on the determined parameter(s) associated with the ultrasound transducer. In some embodiments, the treatment procedure involves utilization of the microbubbles; the system further includes means for providing microbubbles to the target region for initializing the treatment procedure. For example, an administration system may be employed to administer the microbubbles to the target region. Additionally or alternatively, the ultrasound transducer may transmit ultrasound pulses to the target region so as to generate the microbubbles. In addition, the controller may be further configured to perform step (c) only after a focusing property of the acoustic beam at the target region is optimized.

In various embodiments, the system further includes means for detecting the characteristic of the microbubbles in the target region, one of the regions in the tissue-sensitivity map and/or a dedicated monitored region (e.g., a region that is continuously monitored throughout the treatment procedure). The means for detecting the microbubble characteristic may include the ultrasound transducer, an acoustic-signal detection device and/or the second ultrasound transducer different from the ultrasound transducer activated in step (c). In addition, the controller may be further configured to determine the parameter(s) associated with the ultrasound transducer based at least in part on the detected microbubble characteristic. In one embodiment, the generated acoustic beam causes cavitation of at least some of the microbubbles in the selected interaction region(s) in the tissue-sensitivity map. The controller may be further configured to determine the parameter(s) associated with the ultrasound transducer so as to select the microbubbles for cavitation.

In addition, the system may further include an imaging device for acquiring digital representations including multiple voxels of one or more portions of the regions in the tissue-sensitivity map; the controller may be further configured to generate the tissue-sensitivity map based at least in part on the digital representations. In some embodiments, the controller is further configured to determine an anatomical characteristic (e.g., a tissue type, a location, a size, or a function) of the portion(s) of the regions in the tissue-sensitivity map based on the digital representations; the tissue-sensitivity map is then generated based at least in part on the anatomical characteristic. In addition, the controller may be further configured to generate the tissue-sensitivity map by assigning a sensitivity score to voxels of the portion(s) of the regions in the tissue-sensitivity map based at least in part on the anatomical characteristic associated therewith; the sensitivity score indicates a sensitivity level of the voxel to the interaction of the acoustic beam with the microbubbles. The selected interaction region(s) in the tissue-sensitivity map may have a relatively low sensitivity score than the other ones of the regions in the tissue-sensitivity map. In addition, the controller may be further configured to adjust the parameter(s) associated with the ultrasound transducer based at least in part on the sensitivity scores assigned to the regions in the tissue-sensitivity map. In one embodiment, the controller is further configured to adjust the parameter(s) associated with the ultrasound transducer so as to cause at least some of the microbubbles to move from the target region to the selected interaction region(s) in the tissue-sensitivity map.

In another aspect, the invention relates to a method of regulating microbubbles in a treatment procedure for a target region. In various embodiments, the method includes (a) generating a tissue-sensitivity map including multiple regions, one or more of the regions being outside the target region; (b) selecting one or more interaction regions based at least in part on the tissue-sensitivity map; and (c) activating the ultrasound transducer so as to generate an acoustic beam for interacting with the microbubbles in the selected interaction region(s) in the tissue-sensitivity map, thereby indirectly changing a characteristic of the microbubbles (e.g., the amount, concentration, size distribution and/or response of the microbubbles to the acoustic beam) at the target region. In one implementation, the tissue-sensitivity map assigning, to each of the regions, a sensitivity level indicative of tissue sensitivity (e.g., thermal sensitivity and/or sensitivity to microbubble cavitation) to an interaction between the microbubbles and an acoustic beam.

The method may further include determining one or more parameters (e.g., a frequency, an amplitude and/or a phase) associated with one or more transducer elements of the ultrasound transducer based at least in part on the selected interaction region(s) in the tissue-sensitivity map. The ultrasound transducer may then be activated based at least in part on the determined parameter(s). In addition, the treatment procedure may involve utilization of the microbubbles; the method may further include providing microbubbles to the target region for initializing the treatment procedure. In one embodiment, the microbubbles are administered utilizing an administration system. Additionally or alternatively, the method may further include causing the ultrasound transducer to transmit ultrasound pulses to the target region so as to generate the microbubbles. In one embodiment, step (c) is performed only after a focusing property of the acoustic beam at the target region is optimized.

In various embodiments, the method further includes detecting the characteristic of the microbubbles at the target region, one of the regions in the tissue-sensitivity map and/or a dedicated monitored region (e.g., a region that is continuously monitored throughout the treatment procedure). The microbubble characteristic may be detected using the ultrasound transducer, an acoustic-signal detection device and/or the second ultrasound transducer different from the ultrasound transducer activated in step (c). In addition, the method may further include determining the parameter(s) associated with the ultrasound transducer based at least in part on the detected microbubble characteristic. In one embodiment, the generated acoustic beam causes cavitation of at least some of the microbubbles in the selected interaction region(s) in the tissue-sensitivity map. The method may then further include determining the parameter(s) associated with the ultrasound transducer so as to select the microbubbles for cavitation.

In addition, the method may further include acquiring digital representations including multiple voxels of one or more portions of the regions in the tissue-sensitivity map; the tissue-sensitivity map is generated based at least in part on the digital representations. In some embodiments, the method further includes determining an anatomical characteristic (e.g., a tissue type, a location, a size, or a function) of the portion(s) of the regions in the tissue-sensitivity map based on the digital representations; the tissue-sensitivity map is generated based at least in part on the anatomical characteristic. In addition, the method may further include assigning a sensitivity score to voxels of the portion(s) of the regions in the tissue-sensitivity map based at least in part on the anatomical characteristic associated therewith; the sensitivity score indicates a—sensitivity level of the voxel to the interaction of the acoustic beam with the microbubbles. The selected interaction region(s) in the tissue-sensitivity map may have a relatively low sensitivity score than the other ones of the regions in the tissue-sensitivity map. In addition, the method may further include adjusting the parameter(s) associated with the ultrasound transducer based at least in part on the sensitivity scores assigned to the regions in the tissue-sensitivity map. In one embodiment, the method further includes causing movement of at least some of the microbubbles from the target region to the selected interaction region(s) in the tissue-sensitivity map.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1A:
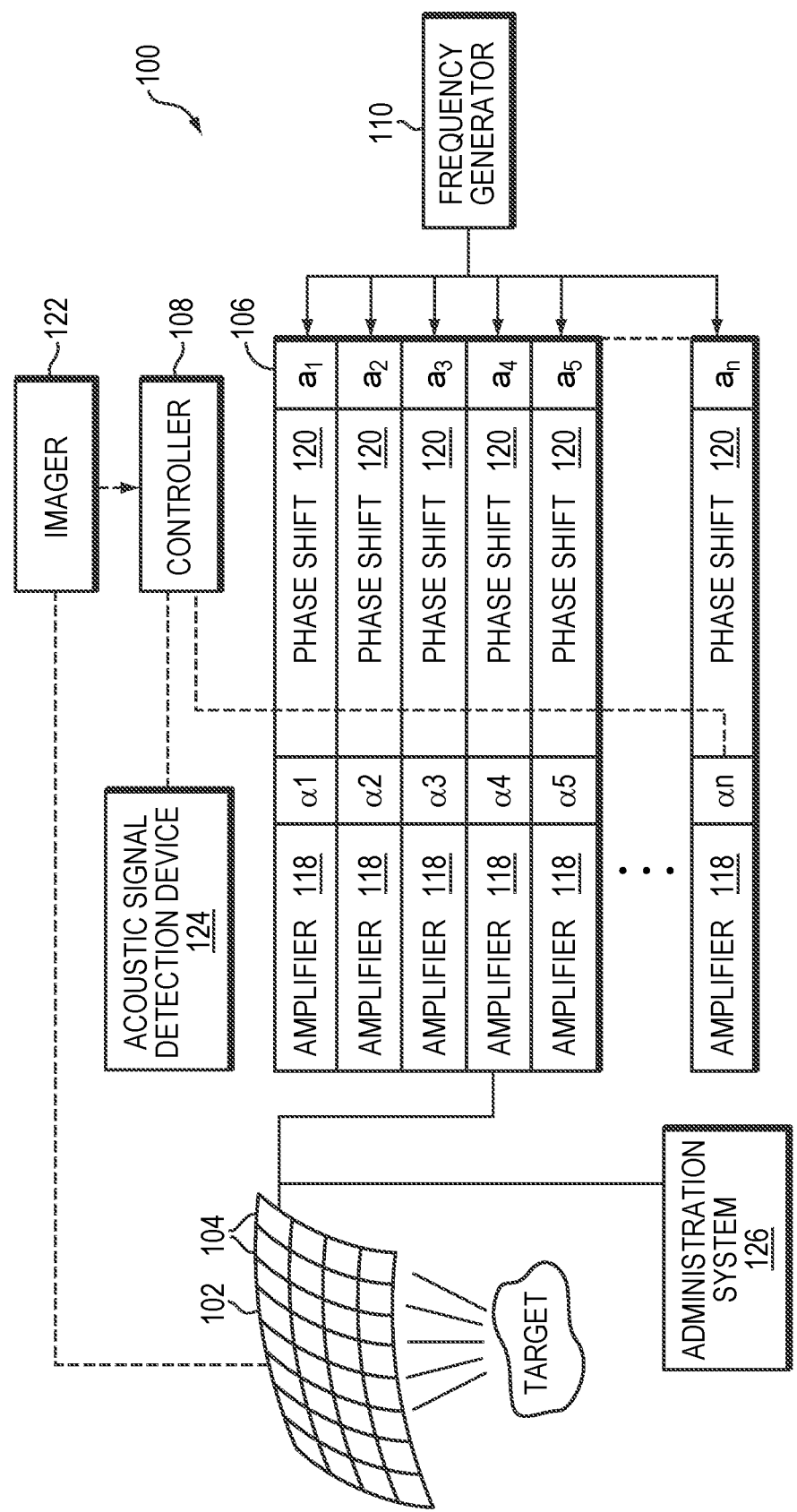
FIG. 1A schematically depicts an exemplary ultrasound system in accordance with various embodiments of the current invention.

FIG. 1A illustrates an exemplary ultrasound system 100 for generating and delivering a focused acoustic energy beam to a target region for disrupting and/or ablating the tissue therein. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) shape suitable for placing it on the surface of the patient's body, or may include one or more planar or otherwise shaped sections. Its dimensions may vary between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each including or consisting of an amplifier 118 and a phase delay circuit 120; each drive circuit drives one of the transducer elements 104. The beamformer 106 receives a radiofrequency (RF) input signal, typically in the range from 0.1 MHz to 10 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radiofrequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $\alpha_1$-$\alpha_n$ imposed by the beamformer 106 serve to transmit and focus ultrasonic energy onto the target region, and account for wave distortions induced in the tissue located between the transducer elements 104 and the target region. The amplification factors and phase shifts are computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, in order to determine the phase shifts and amplification factors necessary to obtain a desired focus or any other desired spatial field patterns at the target region. In certain embodiments, the computation is based on detailed information about the characteristics (e.g., structure, thickness, density, etc.) of the intervening tissue located between the transducer element 104 and the target and their effects on propagation of acoustic energy. Such information may be obtained from an imager 122. The imager 122 may be, for example, a magnetic resonance imaging (MRI) device, a computer tomography (CT) device, a positron emission tomography (PET) device, a single-photon emission computed tomography (SPECT) device, or an ultrasonography device. Image acquisition may be three-dimensional (3D) or, alternatively, the imager 122 may provide a set of two-dimensional (2D) images suitable for reconstructing a three-dimensional image of the target region and/or other regions (e.g., the region surrounding the target). In addition, the ultrasound system 100 and/or imager 122 may be utilized to detect the microbubble response, presence, amount, concentration and/or size distribution, and/or the presence, type, and/or location associated with microbubble cavitation as further described below. Additionally or alternatively, the system may include an acoustic-signal detection device (such as a hydrophone or suitable alternative) 124 that detects transmitted or reflected ultrasound from the microbubbles for measuring the microbubble response presence, amount, concentration and/or size distribution and/or information associated with microbubble cavitation, and which may provide the signals it receives to the controller 108 for further processing. In addition, the ultrasound system 100 may include an administration system 126 for parenterally introducing the microbubbles and/or a therapeutic agent into the patient's body as further described below. The imager 122, the acoustic-signal detection device 124, and/or the administration system 126 may be operated using the same controller 108 that facilitates the transducer operation; alternatively, they may be separately controlled by one or more separate controllers intercommunicating with one another.

Figure 1B:
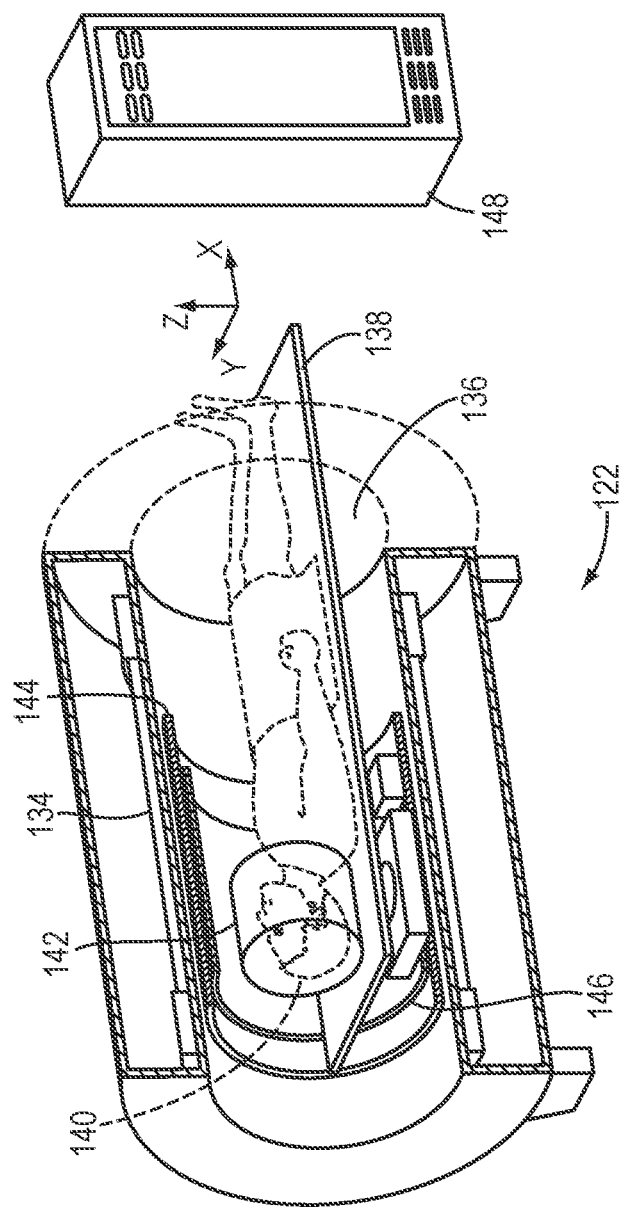
FIG. 1B schematically depicts an exemplary MRI system in accordance with various embodiments of the current invention.

FIG. 1B illustrates an exemplary imager—namely, an MRI apparatus 122. The apparatus 122 may include a cylindrical electromagnet 134, which generates the requisite static magnetic field within a bore 136 of the electromagnet 134. During medical procedures, a patient is placed inside the bore 136 on a movable support table 138. A region of interest 140 within the patient (e.g., the patient's head) may be positioned within an imaging region 142 wherein the electromagnet 134 generates a substantially homogeneous field. A set of cylindrical magnetic field gradient coils 144 may also be provided within the bore 136 and surrounding the patient. The gradient coils 144 generate magnetic field gradients of predetermined magnitudes, at predetermined times, and in three mutually orthogonal directions. With the field gradients, different spatial locations can be associated with different precession frequencies, thereby giving an MR image its spatial resolution. An RF transmitter coil 146 surrounding the imaging region 142 emits RF pulses into the imaging region 142 to cause the patient's tissues to emit magnetic-resonance (MR) response signals. Raw MR response signals are sensed by the RF coil 146 and passed to an MR controller 148 that then computes an MR image, which may be displayed to the user. Alternatively, separate MR transmitter and receiver coils may be used. Images acquired using the MRI apparatus 122 may provide radiologists and physicians with a visual contrast between different tissues and detailed internal views of a patient's anatomy that cannot be visualized with conventional x-ray technology.

The MRI controller 148 may control the pulse sequence, i.e., the relative timing and strengths of the magnetic field gradients and the RF excitation pulses and response detection periods. The MR response signals are amplified, conditioned, and digitized into raw data using a conventional image-processing system, and further transformed into arrays of image data by methods known to those of ordinary skill in the art. Based on the image data, the target region (e.g., a tumor or a target BBB) can be identified.

To perform targeted drug delivery or tumor ablation, it is necessary to determine the location of the target region with high precision. Accordingly, in various embodiments, the imager 122 is first activated to acquire images of the target region and/or non-target region (e.g., the healthy tissue surrounding the target region, the intervening tissue located between the transducer array 102 and the target region and/or any regions located near the target) and, based thereon, determine anatomical characteristics (e.g., the tissue type, location, size, thickness, density, structure, shape, vascularization) associated therewith. For example, a tissue volume may be represented as a 3D set of voxels based on a 3D image or a series of 2D image slices and may include the target region and/or non-target region.

Figure 2A:
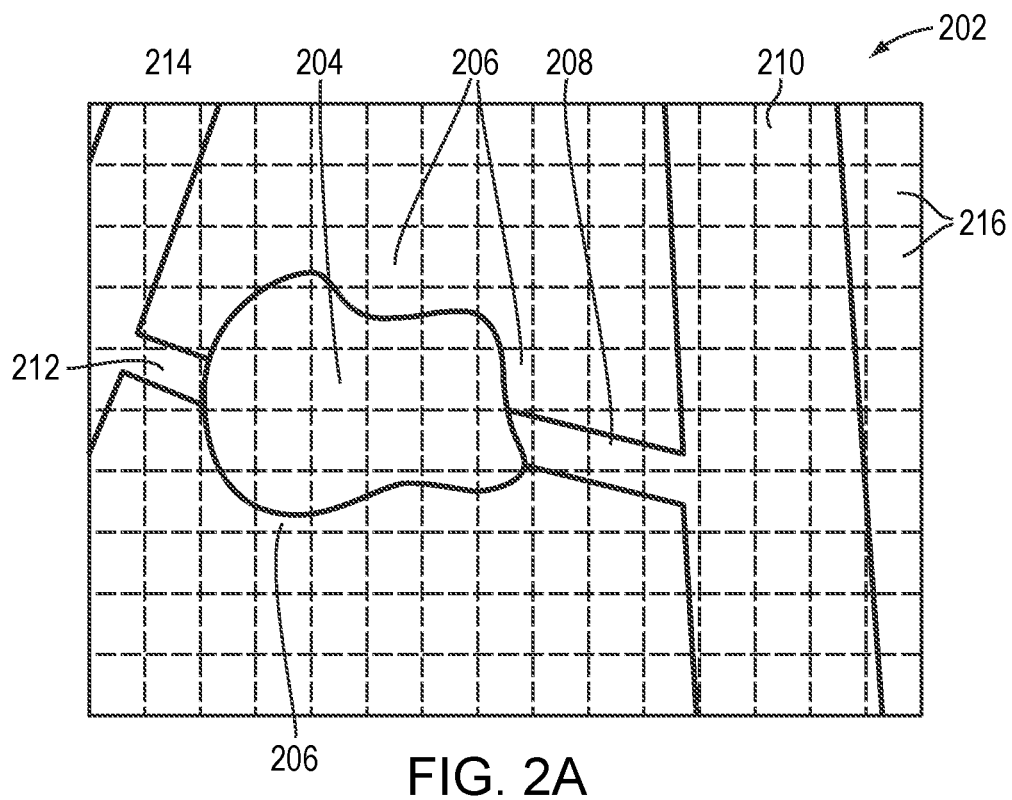
FIG. 2A depicts tissue volumes of the target region and non-target region represented as 3D sets of voxels in accordance with various embodiments of the current invention.

In various embodiments, based on the acquired images and anatomical characteristics, an image, a table or a "map" of the tissue sensitivity level to an effect resulting from interaction between the acoustic beam and microbubbles (e.g., a temperature increase resulting from the acoustic power and/or microbubble cavitation) at the target and/or the non-target tissue can be created as described below. For ease of reference, the following description only refers to a tissue-sensitivity map; it should be understood, however, that a table or other suitable forms of data organization may be used to indicate the tissue sensitivity level. Referring to FIG. 2A, a tissue-sensitivity map 202 may include various regions outside a target region 204. For example, the target region 204 may be a brain tumor and the tissue-sensitivity map 202 may include a region 206 surrounding the target tumor 204, an arteriole 208, a carotid artery 210, a facial vein 212 and a jugular vein 214; each region is represented by one or more voxels 216. In one implementation, the tissue-sensitivity map 202 includes the target region 204 as well. This tissue-sensitivity map 202 generally facilitates treatment planning so that ultrasound is directed effectively at one or more regions outside the target region 204 for clearing microbubbles but without damaging non-target tissue of varying sensitivities. For purposes hereto, the tissue-sensitivity map 202 identifies low-sensitivity non-target regions where the microbubbles, after being utilized for ultrasound autofocusing, may be quickly "destroyed" (i.e., caused to undergo cavitation) or reduced by sonication so as not to delay continued ultrasound treatment of the target 204 (e.g., ablating the target tumor tissue).

The tissue-sensitivity map may be created based on various tissue properties, such as the tissue type. For example, brain tissue may have a lower threshold of thermal damage than bone tissue. Accordingly, in one embodiment, brain tissue is classified in a higher-sensitivity category and/or assigned a higher sensitivity score; whereas bone tissue is classified in a lower-sensitivity category and/or given a lower sensitivity score. Similarly, muscle tissue may have a lower threshold of thermal damage than fatty tissue; thus, muscle tissue may be assigned a relatively high sensitivity score and/or classified in a higher-sensitivity category; whereas fatty tissue is assigned a relatively low sensitivity score and/or classified in a lower-sensitivity category. Thresholds of thermal and/or cavitation damage to various tissue types may be acquired based on retrospective study of the patients experiencing the ultrasound procedure and/or from known literature (see, e.g., www.ncbi.nlm.nih-.gov/pmc/articles/PMC3609720/). In some embodiments, classification and/or assignment of the sensitivity score to various types of tissue is based on the heat capacity of the tissue, which, again, can be acquired from known literature (see, e.g., itis.swiss/virtual-population/tissue-properties/database/heat-capacity/). Because tissue having a relatively low heat capacity may reach a threshold temperature (e.g., 43° C.) and experience damage within a relatively short time period, tissue having a relatively low heat capacity may be classified to a higher-sensitivity category and/or assigned a higher-sensitivity score in terms of acoustic power and/or microbubble cavitation. In one embodiment, the sensitivity score is assigned to each voxel of the target and/or non-target tissue on the tissue-sensitivity map 202.

Additionally or alternatively, the tissue-sensitivity map 202 may be based at least in part on the tissue size and conformation. For example, the diameters of the carotid artery 210 and jugular vein 214 are larger than those of the arteriole 208 and facial vein 212; therefore, microbubble cavitation in the carotid artery 210 or jugular vein 214 may cause less undesired tissue damage than in the arteriole 208 or facial vein 212. Thus, the carotid artery 210 and jugular vein 214 may be classified in a relatively low-sensitivity category and/or assigned a relatively low sensitivity score to microbubble cavitation; whereas the arteriole 208 and facial vein 212 are assigned a relatively high sensitivity score and/or classified in a higher-sensitivity category.

In various embodiments, the tissue-sensitivity map may be further based on the importance of the function associated with the tissue; that is, a given absolute amount of tissue damage may be more acceptable in some tissues than others. For example, if damage to the tissue (e.g., heart tissue) risks being lethal, then even a small amount of damage is unacceptable, and the tissue is assigned a high sensitivity score and/or classified in a high-sensitivity category. In contrast, if even considerable damage to certain tissue (e.g., skin tissue) is unlikely to have significant adverse clinical consequences, the tissue may be assigned a low sensitivity score and/or classified in a low-sensitivity category. Additionally, the tissue-sensitivity map 202 be based on the location of the tissue. For example, tissue located in proximity to an important organ may be assigned a higher sensitivity score and/or classified in a high-sensitivity category; as the distance between the tissue and the important organ increases, the corresponding sensitivity score/category may decrease as well. For ease of reference, the following description refers to a tissue-sensitivity map including tissue of the target and/or non-target regions (e.g., regions outside the target region) with assigned sensitivity scores; it should be understood, however, that the tissue-sensitivity map 202 may include tissue of the target and/or non-target regions with classification categories as well.

Figure 2B:
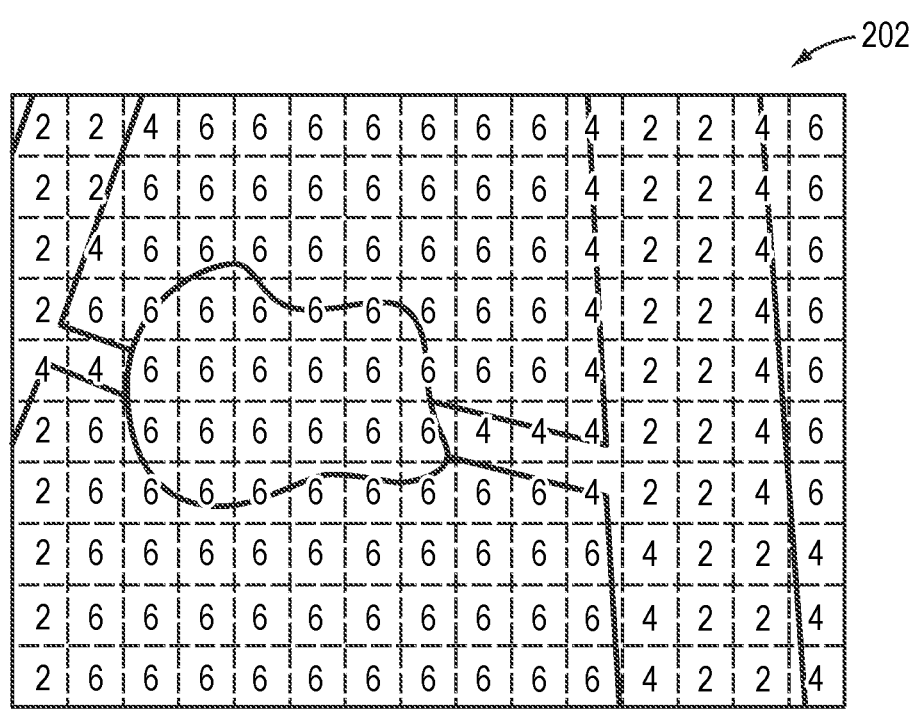
FIGS. 2B-2F depict exemplary tissue-sensitivity maps in accordance with various embodiments of the current invention.
Figure 2C:
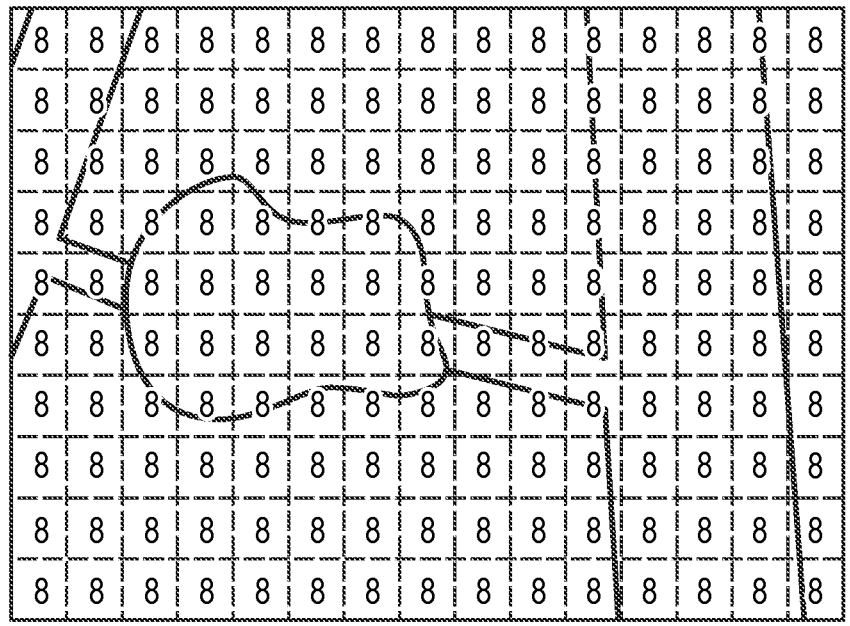
Figure 2D:
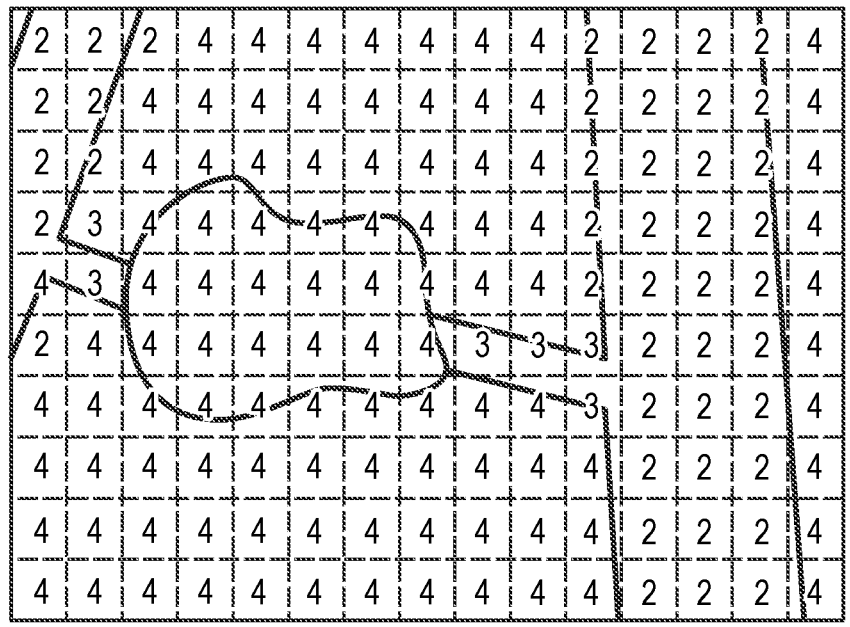
Figure 2E:
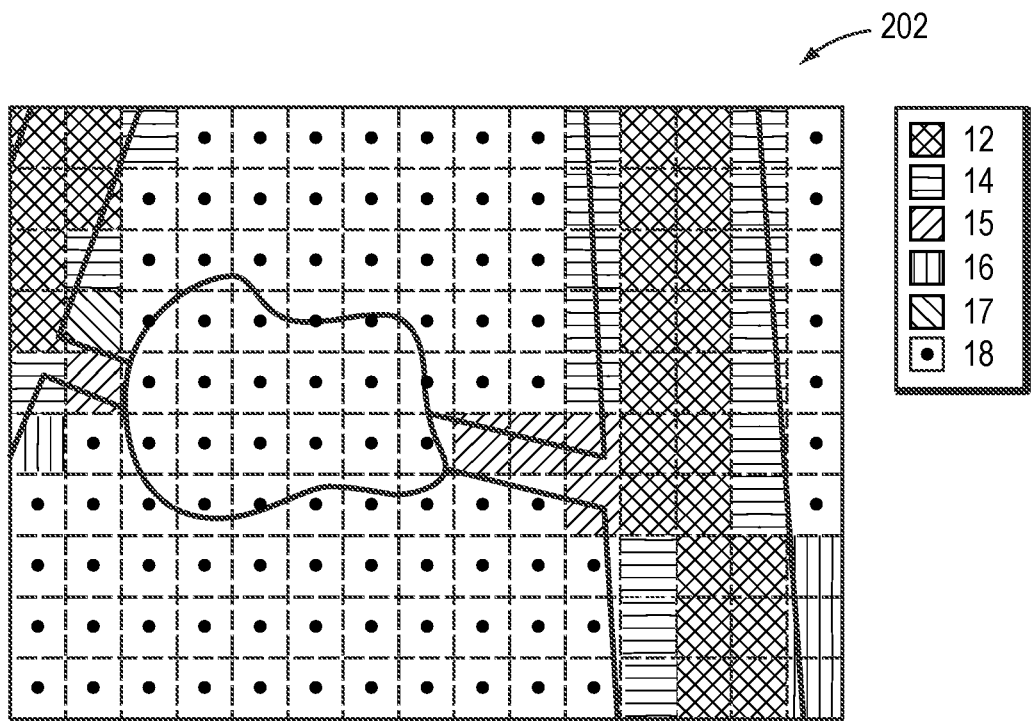

In one embodiment, the sensitivity scores assigned to each voxel of the target and/or non-target tissue based on various tissue properties (e.g., type, size, function, location, etc.) are summed to create a tissue-sensitivity map. For example, FIGS. 2B-2D depict the tissue-sensitivity maps in which the sensitivity score assigned to each voxel is based on the tissue type, function, and size, respectively. FIG. 2E depicts the sum of the sensitivity scores assigned to the voxel based on its corresponding tissue type, function and size as shown in FIGS. 2B-2D. For example, the artery 210 and jugular vein 214 correspond to a lower summed sensitivity score (e.g., 12) than the arteriole 208 and facial vein 212; and the summed sensitivity score (e.g., 15) of the arteriole 208 and facial vein 212 is lower than that (e.g., 18) of the target tumor region 204 and its surrounding region 206. The tissue-sensitivity map 202 may be stored in system memory prior to, during or after the microbubble-mediated ultrasound focusing procedure for regulating the microbubble concentration and/or amount in the target/non-target tissue as further described below.

Figure 2F:
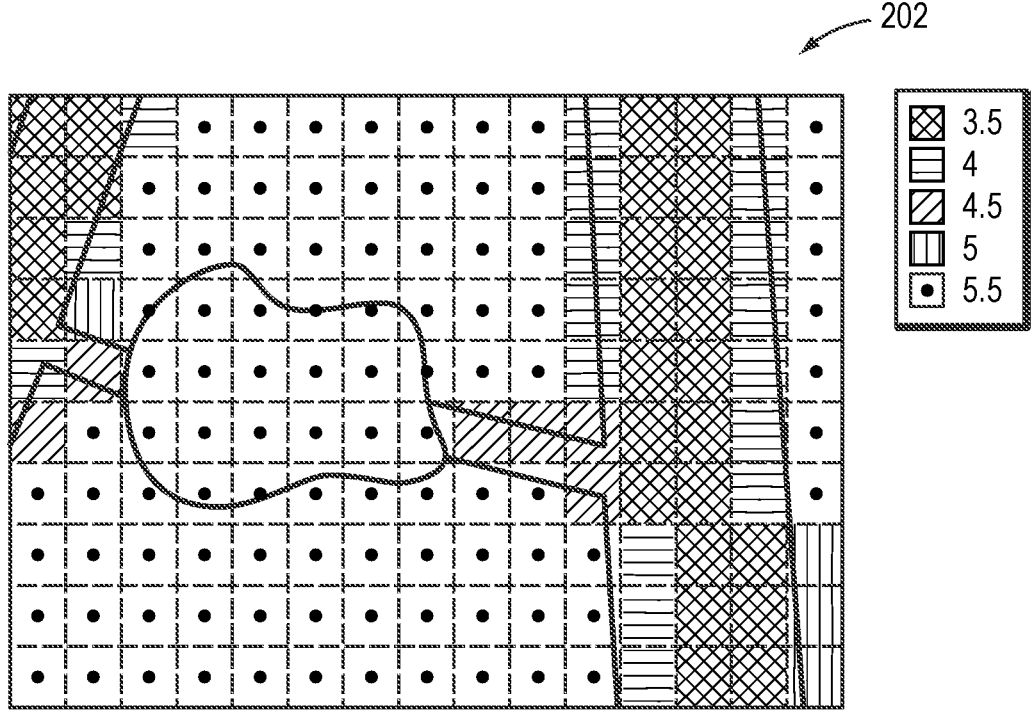

Alternatively, the sensitivity score assigned to the voxel based on its corresponding tissue properties (e.g., type, size and conformation, function, location, etc.) may be averaged, and the average may be weighted or otherwise adjusted to reflect the degree of importance of the various tissue characteristics. For example, because brain tissue, arteriole and artery all have high sensitivity levels to the temperature increase caused by acoustic power and/or microbubble cavitation and their functionalities are all equally important, the region(s) where the microbubble are to be destroyed may mainly depend on the size of the tissue. Thus, the sensitivity scores assigned based on the tissue type (as shown in FIG. 2B) and the function (as shown in FIG. 2C) may both have a weighting factor of 25%; whereas the sensitivity scores assigned based on the size (as shown in FIG. 2D) may have a weighting factor of 50%. FIG. 2F depicts the sensitivity map having the weighted tolerance scores. It should be noted that in this approach, the absolute value of the sensitivity score is not critical so long as at least one region outside the target region 204 on the tissue-sensitivity map has a sensitivity score lower than the target region 204, indicative of a lower sensitivity level to the applied acoustic power and/or microbubble cavitation; the relative lower sensitivity score may be sufficient to facilitate treatment planning and/or indirectly reduce microbubbles at the target region 204 as further described below.

Figure 3:
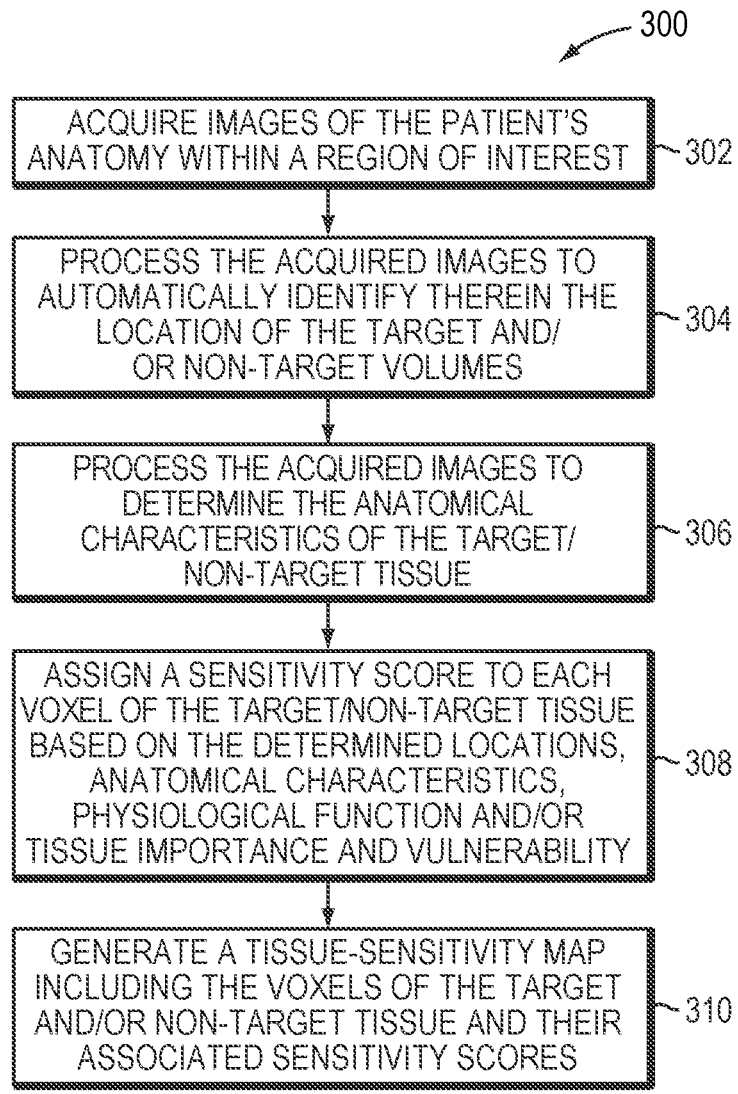
FIG. 3 is a flow chart illustrating an exemplary approach for generating a tissue-sensitivity map in accordance with various embodiments of the current invention.

FIG. 3 is a flow chart illustrating an exemplary approach 300 for creating the tissue-sensitivity map in accordance with various embodiments. In a first step 302, an imaging apparatus is activated to acquire images of the patient's anatomy within a region of interest. The images may be 3D images or a set of 2D image slices suitable for reconstructing 3D images of the anatomic region of interest. In a second step 304, the images are processed by a controller associated with the imaging apparatus to automatically identify therein the location of the target and/or non-target volumes using suitable image-processing techniques. In one embodiment, the tissue volume of the target and/or non-target is represented as a 3D set of voxels. In a third step 306, the controller may further process the images to determine the anatomical characteristics (e.g., the type, size, property, structure, thickness, density, etc.) of the target/non-target tissue based on an anatomical map and particular properties of the tissue (e.g., density and hydration) revealed in the images. In a fourth step 308, based on the determined location, anatomical characteristics and physiological function (and, in some embodiments, known literature bearing on tissue importance and vulnerability), the controller may assign a sensitivity score to each voxel of the target/non-target tissue indicating the tissue's sensitivity level to an effect resulting from the interaction between the applied sonications and microbubbles (e.g., a temperature increase resulting from the applied acoustic power and/or microbubble cavitation). If multiple sensitivity scores are assigned to a voxel based on different tissue characteristics (e.g., types, sizes, locations, functions, etc.), the sensitivity scores associated with the voxel may be summed or averaged, and the average may be weighted or otherwise adjusted to reflect the degrees of importance of the various tissue characteristics. In a fifth step 310, the tissue-sensitivity map including the voxels of the non-target regions, such as regions outside the target region, (and, in some embodiments, the target region) and their corresponding sensitivity scores may be generated.

In various embodiments, prior to and/or during an ultrasound procedure for treating the target (e.g., applying sonications to ablate the target tissue), a small cloud of transient microbubbles is provided to the target region for autofocusing an acoustic beam therein. The microbubbles may be generated using the ultrasound pulses and/or introduced intravenously using the administration system 126. Microbubble characteristics (e.g., the presence, concentration and/or amount) and/or behavior or response (e.g., cavitation) are monitored using the acoustic-signal detection device 124 and/or the transducer array 102. Approaches for autofocusing an ultrasound beam at the target region are provided, for example, in International Applications No. PCT/IB2017/000990 (filed on Jul. 19, 2017) and U.S. patent application Nos. 62/781,258 (filed on Dec. 18, 2018); approaches for providing microbubbles to the target region are provided, for example, in International Applications No. PCT/IB2019/001537 (filed on Dec. 5, 2018); approaches for measuring the characteristics and/or activities of microbubbles are provided, for example, in U.S. Patent Publication No. 2018/0206816 and International Application Nos. PCT/IB2018/000841 (filed on Jun. 29, 2018) and PCT/IB2018/000774 (filed on May 22, 2018); and approaches to configuring the transducer array 102 for detecting microbubble responses are provided, for example, in U.S. Patent Application No. 62/681,282 (filed on Jun. 6, 2018). The entire contents of these applications are incorporated herein by reference.

Figure 4A:
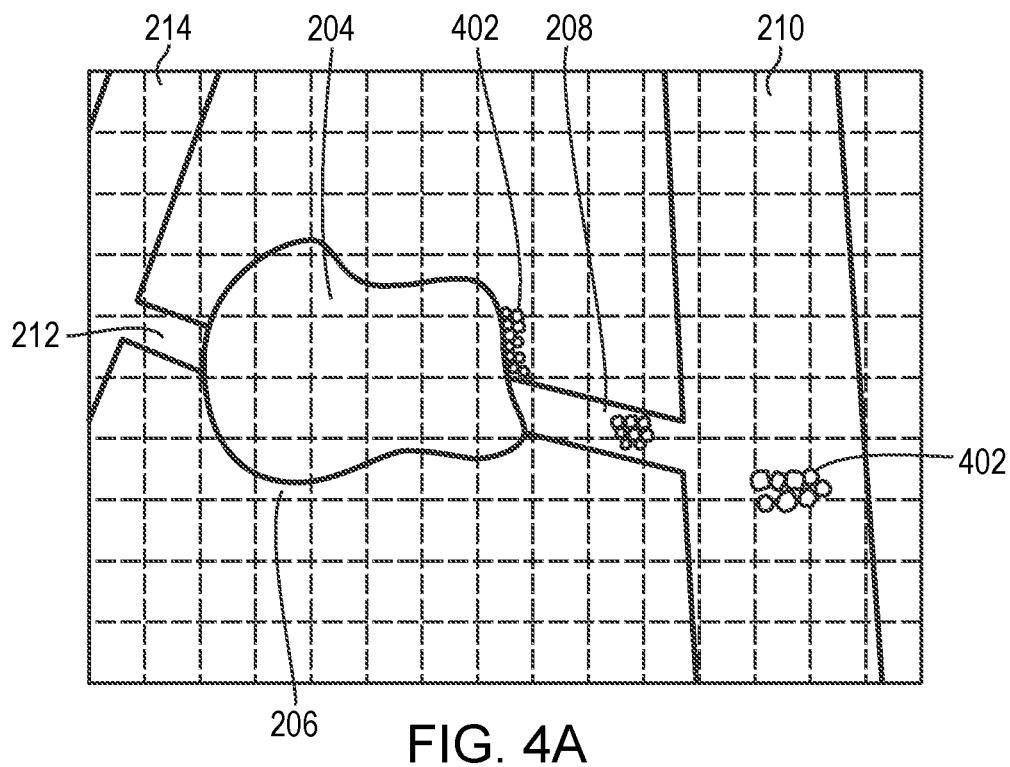
FIGS. 4A-4C depicts various microbubble-regulating approaches for indirectly eliminating/reducing a microbubble population at a target region or its nearby non-target region in accordance with various embodiments of the current invention.

In one embodiment, after the transducer parameters (e.g., frequencies, phase shifts and/or amplitudes) that optimize the focus at the target region are determined (e.g., via analysis of the acoustic reflections from the microbubbles) in the autofocusing procedure, the amount of microbubbles at the target region (and/or nearby non-target region) is preferably limited so as to avoid undesired damage to non-target tissue during ablation of the target tissue. Accordingly, after the autofocusing procedure, the presence, amount, concentration and/or size distribution of microbubbles at the target region (and/or nearby non-target region) may be measured based on the acoustic signals transmitted or reflected from the microbubbles using, again, the acoustic-signal detection device 124 and/or transducer array 102. If the microbubbles are present (or, in some embodiments, the amount thereof exceeds a predetermined threshold that effectively precludes clinically significant damage to target and/or non-target tissue), a microbubble-regulating approach may be implemented to eliminate (or at least reduce) microbubbles at one or more selected non-target regions corresponding to low sensitivity levels on the tissue-sensitivity map 202; this may then indirectly reduce the microbubble population at the target and/or its nearby region. For example, referring to FIG. 4A, when the presence or excess microbubbles 402 at the target region 204 are detected, the controller 108 may analyze the reflection signals from microbubbles near the target 204 to identify other tissue regions that also have microbubbles therein. For example, microbubbles may be present in the arteriole 208 and artery 210. The controller 108 may then access the system memory to retrieve the stored tissue-sensitivity map 202, compare the sensitivity levels associated with the regions where microbubbles are present, and select one or more regions to destroy the microbubbles therein. For example, because the artery 210 has a relatively low sensitivity score compared to the target region 204 and the arteriole 208 (as depicted in FIGS. 2E and 2F), the controller 108 may cause the beamformer 106 to provide drive signals to the transducer elements 104 to generate a focus (e.g., a point focus, a line focus or any suitable shape of focus) at microbubbles 402 in the artery 210 so as to cause cavitation thereof, thereby reducing the microbubble concentration/amount before they reach the target region 204. Because this approach may effectively reduce the overall amount of microbubbles in the bloodstream, the amount/concentration of microbubbles in the target region 204 (as well as everywhere else in the bloodstream) can be indirectly reduced. As a result, undesired damage resulting from the microbubbles at non-target tissue during a subsequent ultrasound procedure (e.g., ablating the target tissue) may be avoided. Again, the ultrasound parameter values (e.g., amplitudes, phases and/or frequencies) for creating the focus and causing microbubble cavitation at the selected region(s) may be computed by the controller 108 based on anatomic characteristics acquired using the imager 122 as described above. In addition, the controller 108 may be configured to automatically create the focus and adjust the ultrasound intensity to start the microbubble-regulating processes after the ultrasound autofocusing procedure is complete, when the presence of the microbubbles in the target region 204 is detected and/or when the number of the microbubbles 402 in the target region 204 exceeds the predetermined threshold during or after the autofocusing procedure.

It should be noted that the selected region(s) for microbubble cavitation may not necessarily correspond to the lowest sensitivity score(s) on the tissue-sensitivity map; so long as the selected region(s) has a sensitivity score lower than the target region 204, it may be sufficient to destroy microbubbles at the selected region(s) without damaging tissue in the region surrounding the target and/or the selected non-target region(s). In addition, the ultrasound parameter values (e.g., amplitudes, phases and/or frequencies) for causing microbubble cavitation at the selected region(s) may be adjusted based on the corresponding sensitivity score(s). For example, the acoustic power of the beam transmitted to the region that corresponds to the lowest sensitivity score may be relatively large so as to cause a larger amount of microbubble cavitation. In contrast, when the selected region has a sensitivity score that is slightly larger than that of the target region, the acoustic power may be reduced to cause gentle microbubble cavitation, thereby avoiding damage to the selected region.

Figure 4B:
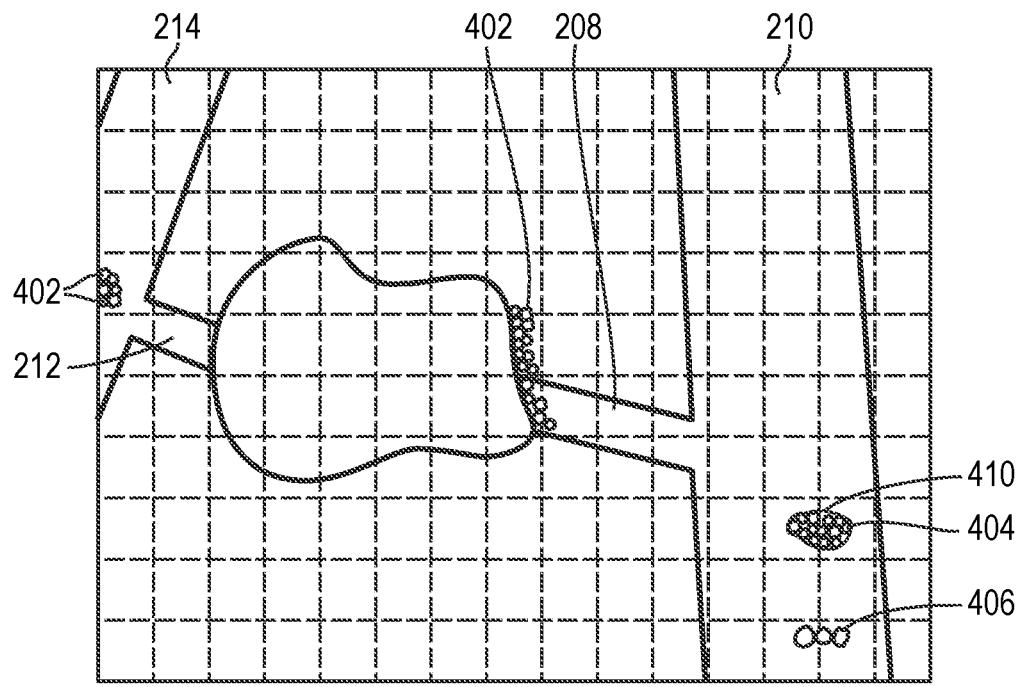

In various embodiments, selection of the region(s) in which microbubbles will be destroyed may be based on the relative location(s) of the region(s) with respect to the target region 204. For example, referring to FIG. 4B, although both the carotid artery 210 and jugular vein 214 have the lowest sensitivity scores on the tissue-sensitivity map 202, it may be preferable to cause microbubble cavitation in the artery 210 rather than in the jugular vein 214. This is because the artery 210 is located upstream of the target region 204; destroying the microbubbles therein may promptly reduce the microbubble population in the target 204, whereas the jugular vein 214 is downstream of the target region 204, and therefore it may take longer for the microbubble concentration at the target to be reduced when microbubbles are destroyed in the jugular vein 214.

Additionally or alternatively, the amount of microbubbles present in the regions on the tissue-sensitivity map 202 may be taken into account when selecting the region(s) for microbubble destruction. For example, referring again to FIG. 4B, although both regions 404, 406 are located in the artery 210 and upstream of the target 204, because more microbubbles are present in the region 404 than the region 406, it may be preferable to apply the focused acoustic beam to the region 404 as this may result in more microbubble cavitation, and therefore more efficient reduction of the microbubble population in the target region (and everywhere else in the bloodstream). The amount of microbubbles in various regions may be measured based on acoustic reflections from the microbubbles using the transducer array 102 and/or acoustic signal detection device 124 as described above.

Figure 4C:
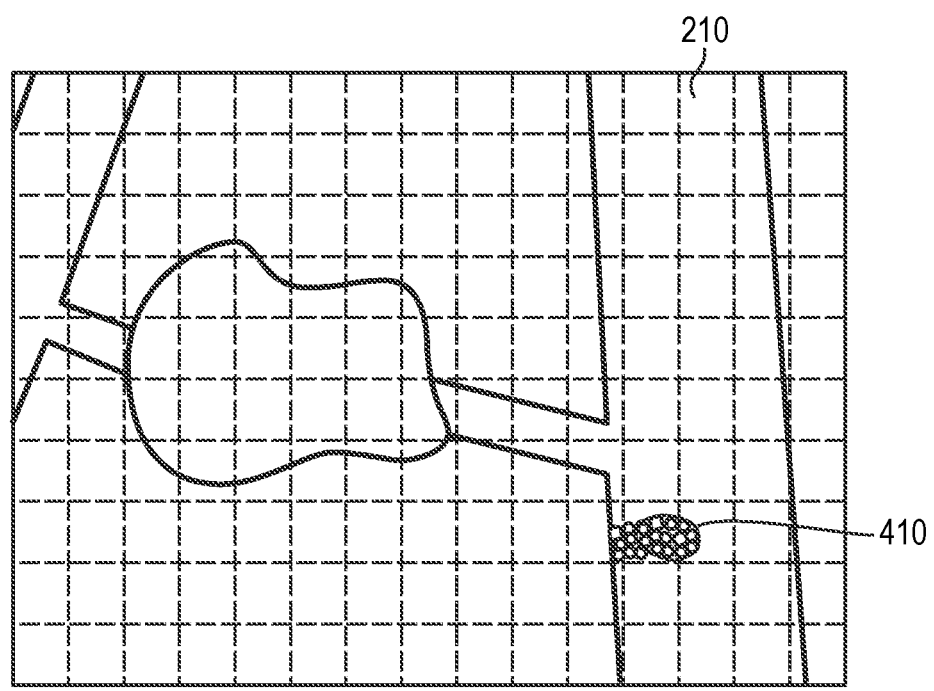

In various embodiments, properties of the focused beam are optimized based on the characteristics of the microbubbles. For example, referring again to FIG. 4B, the size and/or shape of the focus 410 may be adjusted to conform to the size and/or shape of the microbubbles that are to be cleared. In this way, the microbubble-regulating process may efficiently destroy the selected microbubbles at once. Alternatively, the focus may be shaped/sized to destroy a portion of the microbubbles only. For example, referring to FIG. 4C, when some of the microbubbles are near the artery wall, cavitation thereof may result in damage to the artery wall; accordingly, the ultrasound controller 108 may shape and size the focus 410 to destroy only a portion of microbubbles that is not in proximity to the artery wall. Adjustment of the focal size and/or shape may be achieved by adjusting the amplification factors and/or the phase shifts of the ultrasound beams transmitted from the transducer elements as described above.

While the main force for distributing microbubbles in the target region and non-target regions outside the target is blood circulation, in some embodiments, the ultrasound transducer can be configured (e.g., by adjusting the phases, amplitudes and/or frequencies) to create a focus that can induce movement of microbubbles by applying an acoustic force thereto. For example, the generated focus may sweep at least a portion of the microbubbles from the target region 204 (or a region having a relatively high sensitivity score) to a lower-sensitivity region (e.g., the facial vein 212) outside the target. In one embodiment, the generated focus has a relatively low acoustic power that is sufficient to sweep the microbubbles 402 without causing cavitation thereof.

In various embodiments, the focus induces movement of microbubbles 402 by applying an acoustic force thereto. The acoustic force is produced by a change in the density of energy and momentum of the propagating ultrasound waves resulting from absorption, scattering or reflection from the intervening tissue located between the transducer 102 and the target region 204. Generally, the amplitude of the acoustic force is proportional to the ultrasound intensity. Accordingly, in one implementation, the intensity of the ultrasound beams directed to the microbubbles 402 gradually increases until the generated acoustic force suffices to manipulate and move the microbubbles 402. In another embodiment, prior to manipulation of the microbubbles 402, the characteristics (e.g., an absorption coefficient) of the intervening tissue are measured using the imager 122 as described above; the intensity of ultrasound beams sufficient for moving the microbubbles 402 can be computed based thereon. Once the microbubbles are moved away from the target region and/or reach the region(s) having a relatively low sensitivity score, the controller 108 may increase the intensity of the ultrasound beams to cause microbubble cavitation in the low-sensitivity region(s). Since the cavitation now occurs in the low-sensitivity region(s), whatever damage may occur will be clinically acceptable. Accordingly, this approach may advantageously allow microbubbles to be removed from the region that is more vulnerable to the ultrasound-induced microbubble cavitation (e.g., higher-sensitivity region) to the region that is less likely to be damaged by the cavitation (e.g., lower-sensitivity region). As a result, unexpected damage of healthy tissue in the target and/or non-target regions may be minimized.

It should be understood that the terms "point focus" and "line focus," as used herein, do not refer to points and lines in the strict mathematical sense, but to focus shapes that approximate a point or line, respectively. Thus, the intensity distribution of a point focus (which may, for example, take the shape of a two-dimensional Gaussian distribution) may be characterized by half-widths in both dimensions of the focal plane on the order of a few acoustic wavelengths, whereas the intensity distribution of a line focus (which may, for example, have a one-dimensional Gaussian profile perpendicular to the line) is extended along the direction of the line, but may have a half-width perpendicular thereto on the order of only a few acoustic wavelengths.

Figure 5:
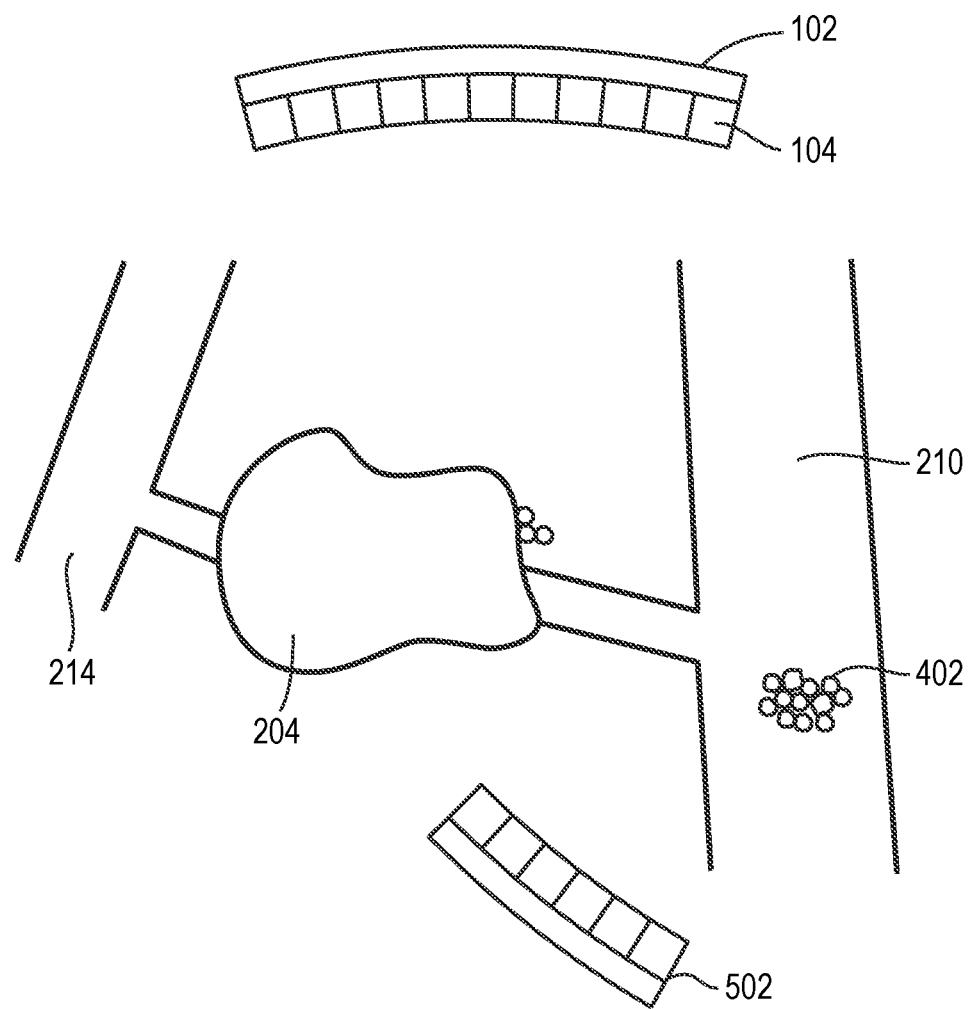
FIG. 5 depicts implementation of the second ultrasound transducer for monitoring the microbubble-regulating approach and/or ultrasound procedure in real time in accordance with various embodiments of the current invention.

In various embodiments, the microbubble characteristic (e.g., the amount, concentration, size distribution, and/or response) during the ultrasound-induced microbubble cavitation at the selected low-sensitivity region(s) and/or during sweeping from the relatively high-sensitivity region toward the relatively low-sensitivity region is monitored in real time using the acoustic-signal detection device 124 and/or the transducer array 102 as described above. In addition, referring to FIG. 5, a second transducer array 502 may be implemented to monitor the cavitation and/or sweep process. For example, when the transducer array 102 is activated to cause microbubble cavitation at the artery 210, the second transducer array 502 may be placed on the skull that is closest to the artery 210 for monitoring the cavitation processes therein. In various embodiments, based on the acoustic signals measured by the acoustic-signal detection device 124, the transducer array 102 and/or the second transducer array 502, the controller 108 may responsively adjust the ultrasound parameter values (e.g., phases, amplitudes and/or frequencies) so as to ensure a desired amount of microbubbles are destroyed without damaging the selected low-sensitivity region(s). For example, if the detected signals indicate that the power of the generated focus does not suffice to cause microbubble cavitation, the controller 108 may increase the intensity of the ultrasound beams. In addition, the controller 108 may adjust the phases of the beams from the transducer elements 104 so as to gradually move the focus to follow the movement of microbubbles (e.g., resulting from the blood circulation) that are to be destroyed in the bloodstream.

In various embodiments, the above described microbubble-regulating processes (either by sweeping microbubbles from a relatively high-sensitivity region to a relatively low-sensitivity region and/or inducing microbubble cavitation in the low-sensitivity region based on the tissue-sensitivity map 202) can be repeated until the microbubble population at the target region 204 is completely eliminated or at least brought below the predetermined threshold; again, this may be verified using images acquired by the imager 112 and/or reflected signals detected by the acoustic-signal detection device 124, transducer array 102 and/or the second transducer array 502. After the desired amount of microbubbles is removed from the target region 204, the controller 108 may energize the transducer elements 104 with treatment parameters (e.g., phases, frequencies, amplitudes, sonication durations, etc.) that are determined during the autofocusing procedure to transmit ultrasound waves to the target region 204 to start or continue treatment.

Although the microbubble-regulating approach described above regulates the microbubble concentration/amount prior to application of the ultrasound pulses/waves for treating the target (e.g., ablating the target tumor), the approach may be applied to eliminate/reduce the microbubbles during and/or after the ultrasound procedure so as to avoid undesired damage to the target/non-target tissue. For example, the target treatment procedure may be commenced after the microbubble population at the target falls below the predetermined threshold; during the treatment procedure, the microbubble concentration and/or response at the target and/or non-target regions may be monitored in real-time using, again, the acoustic-signal detection device 124, transducer array 102 and/or the second transducer array 502. If excess microbubbles (e.g., carried by the bloodstream from another region) are measured, the above-described microbubble-regulating approach may be commenced to eliminate/reduce the excess microbubbles based on the tissue-sensitivity map. For example, referring again to FIG. 5, during treatment, the transducer array 102 may generate a focus at the target region 204 to ablate the tissue therein; the second transducer array 502 may in real-time monitor the microbubble amount/concentration in the artery 210. If excessive microbubbles in the artery 210 are detected, the second transducer array 502 may commence the microbubble-regulating approach to destroy microbubbles in the artery 210 before they enter the target 204. As a result, treatment of the target tissue may be continued without any interruption. Accordingly, various embodiments of the present invention provide approaches to indirectly eliminate/reduce microbubbles at the target region prior to and/or during the ultrasound treatment procedure without prolonging the procedure time while avoiding undesired damage to the healthy, non-target tissue.

In addition, although the ultrasound procedure described herein refers to thermal ablation for treating a benign or malignant tumor within a patient's skull, it should be understood that other ultrasound procedures may generally apply the same microbubble-regulating approach as well for regulating the microbubble concentration/amount at the target/non-target region. For example, the ultrasound procedure may be microbubble-mediated BBB opening or thermal ablation for treating a blood clot within a patient's skull or other body region. Implementing the microbubble-regulating approach may, again, eliminate/reduce undesired microbubbles at the target BBB region or target clot, thereby advantageously providing improved control over the microbubble cavitation for ablation and avoiding damage to non-target tissue. Further, the above description refers to only an ultrasound treatment procedure for ease of reference; it should be understood, that the same approaches generally apply as well to an ultrasound imaging procedure.

Figure 6A:
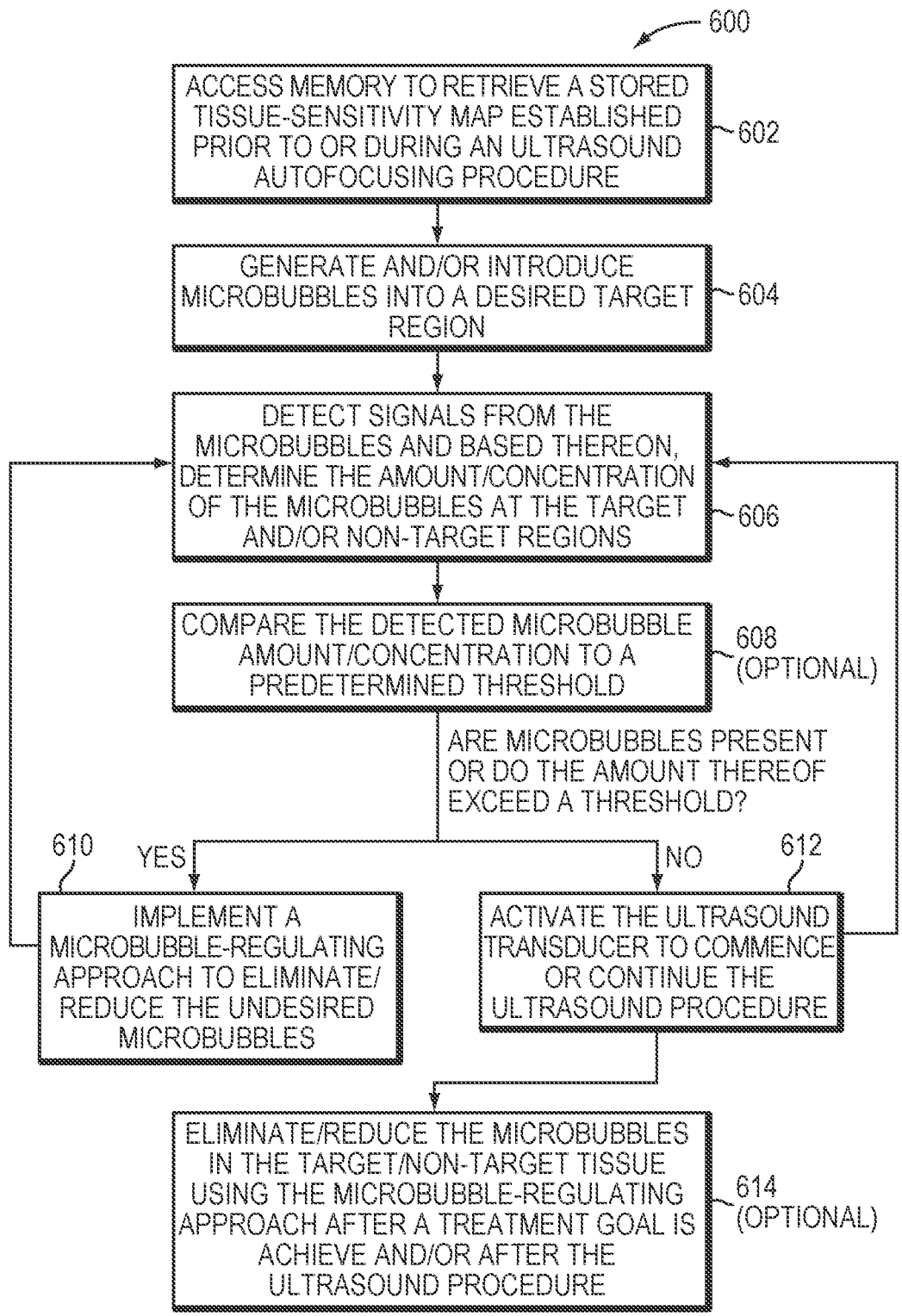
FIG. 6A is a flow chart illustrating an approach for regulating a microbubble population in the target and/or non-target regions prior to, during and/or after an ultrasound procedure in accordance with various embodiments of the current invention.

FIG. 6A is a flow chart illustrating a representative approach 600 in accordance herewith for regulating microbubble concentration/amount prior to, during and/or after an ultrasound procedure in accordance with various embodiments. For example, the microbubble-regulating approach may be implemented after performing ultrasound autofocusing but before ablating the target tissue. In a first step 602, the ultrasound controller 108 accesses the memory to retrieve the stored tissue-sensitivity map established prior to or during the ultrasound focusing procedure. In a second step 604, the microbubbles are generated using the transducer array 102 and/or introduced via the administration system 126. In a third step 606, the acoustic-signal detection device 124, transducer array 102 and/or the second transducer array 502 are activated to detect signals from the microbubbles; based thereon, the amount, concentration and/or response of the microbubbles at the target and/or non-target regions (e.g., regions outside the target region) may be determined. In an optional step 608, the detected microbubble amount/concentration may be compared to a predetermined threshold. If the microbubbles are present at the target region (and/or nearby non-target region) and/or the detected microbubble amount/concentration exceeds the predetermined threshold, a microbubble-regulating approach is implemented to eliminate/reduce the microbubbles (step 610). Steps 606 and 610 are iteratively performed until the microbubble amount/concentration at the target/non-target regions is below the predetermined threshold. Subsequently, the controller 108 may activate the ultrasound transducer 102 to commence or continue the ultrasound procedure (e.g., ablating the target tumor) (in step 612). Steps 606-612 may be iteratively performed throughout the entire ultrasound procedure. In various embodiments, after a treatment goal (e.g., ablating the target tissue) of the ultrasound procedure is achieved, the microbubbles in the target/non-target tissue are optionally eliminated/reduced using, again, the microbubble-regulating approach (in step 614). In one implementation, the microbubbles are eliminated/reduced after the ultrasound procedure only when the measured microbubble amount/concentration exceeds a predetermined threshold.

Figure 6B:
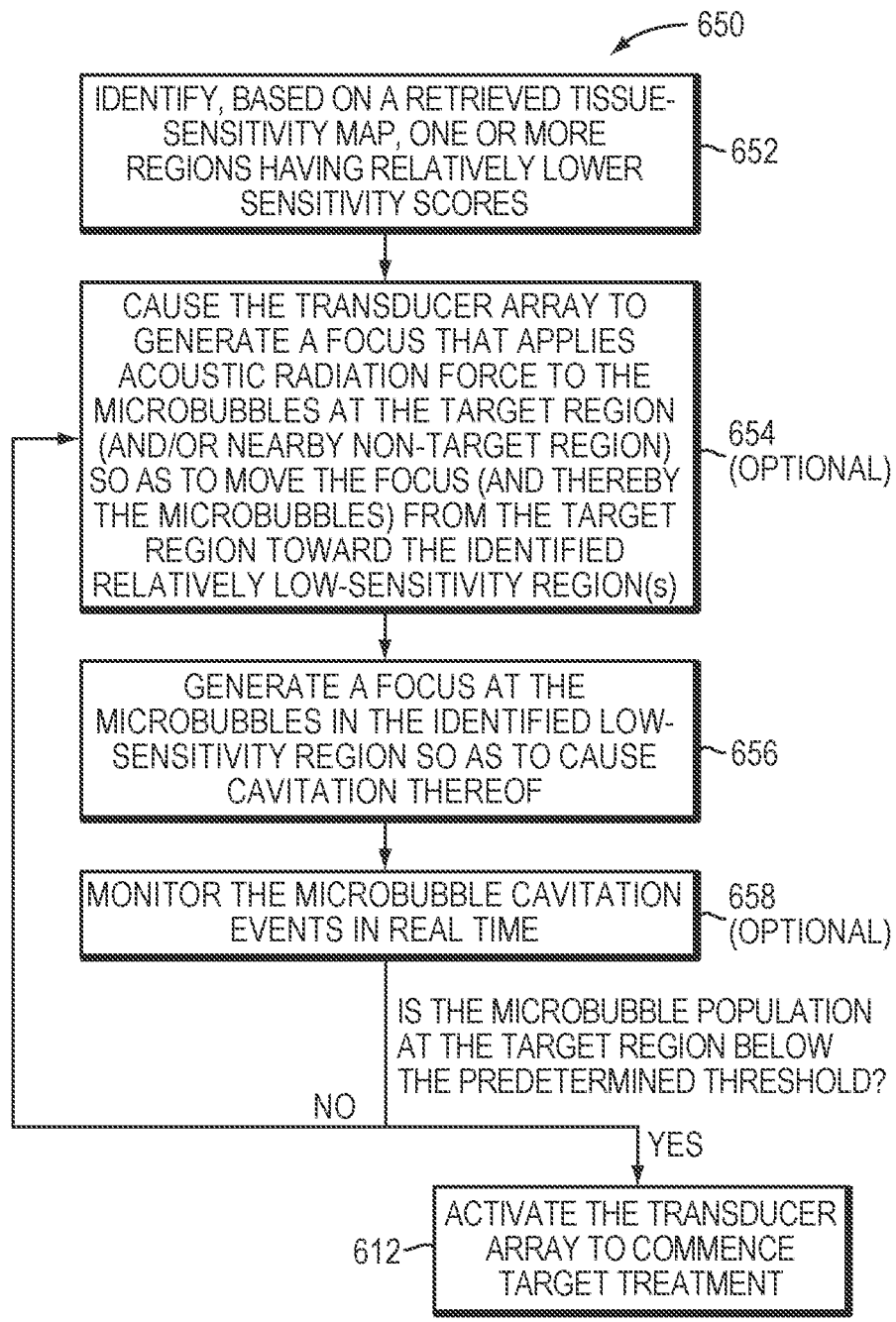
FIG. 6B is a flow chart illustrating an exemplary microbubble-regulating approach in accordance with various embodiments of the current invention.

FIG. 6B is a flow chart illustrating a representative microbubble-regulating approach 650 in accordance herewith. In various embodiments, upon determining that the microbubbles are present at the target region (and/or nearby non-target region) and/or the detected microbubble amount/concentration exceeds the predetermined threshold, the controller 108 may identify, based on the tissue-sensitivity map, one or more regions having relatively low sensitivity scores indicating low sensitivity to a temperature increase resulting from the sonications and/or microbubble cavitation (in step 652). The identified low-sensitivity region(s) may have the lowest sensitivity score in the tissue-sensitivity map. Alternatively, the identified low-sensitivity region(s) may only need to have a sensitivity score lower than that of the target region and/or the region(s) in which the presence of microbubbles or excess microbubbles are detected. In an optional step 654, the controller 108 may cause the transducer array 102 to generate a focus that applies acoustic force to the microbubbles 402 at the target region (and/or nearby non-target region), thereby inducing movement thereof. In addition, the controller 108 may adjust the phases of the beams transmitted from the transducer elements 104 so as to gradually move the focus (and thereby the microbubbles) from the target region toward the identified relatively low-sensitivity region. Optionally, movement of the microbubbles may be monitored in real time using the acoustic-signal detection device 124, transducer array 102 and/or the second transducer array 502 so as to ensure sufficient movement of the microbubbles without cavitation. In a third step 656, the controller 108 may generate a focus at the microbubbles in the identified low-sensitivity region so as to cause cavitation thereof. Optionally, the microbubble cavitation events are monitored in real time using, again, the acoustic-signal detection device 124, transducer array 102 and/or the second transducer array 502 to ensure that no (or at least limited) damage occurred at the relatively low-sensitivity region (step 658). Steps 654-658 may be iteratively performed until the microbubble concentration/amount at the target region (and/or nearby non-target region) is below the predetermined threshold. Once the microbubble concentration/amount is below the predetermined threshold, the ultrasound procedure for treating the target (e.g., ablating the tissue therein) may be commenced (step 612).

In general, functionality for facilitating a microbubble-mediated ultrasound autofocusing procedure and an ultrasound target treatment procedure and/or using a microbubble-regulating approach to eliminate (or at least reduce) microbubbles in the target and/or non-target regions may be structured in one or more modules implemented in hardware, software, or a combination of both, whether integrated within a controller of the imager 122, an ultrasound system 100 and/or the administration system 124, or provided by a separate external controller or other computational entity or entities. Such functionality may include, for example, analyzing imaging data of the target and/or non-target regions acquired using an imager 112, determining a 3D voxel set of the target tissue and/or non-target tissue based on the imaging data, determining the anatomical characteristics (e.g., the tissue type, location, size, thickness, density, structure, shape, vascularization) associated with the target/non-target tissue, assigning a tissue sensitivity score to every voxel of the target/non-target tissue based on the tissue type, location, size, function, etc., causing an acoustic-signal detection device and/or transducer array to detect acoustic signals transmitted or reflected from the microbubbles, determining the microbubble amount, concentration, size distribution and/or response based on the detected acoustic signals, comparing the measured microbubble amount/concentration to a predetermined threshold, identifying a tissue region outside the target that has a relatively low sensitivity score compared to the target region and/or other non-target regions, configuring the ultrasound transducer array to generate a focus at the identified tissue region to cause microbubble cavitation therein, adjusting the ultrasound parameters so as to gradually sweep the excess microbubbles from the target region (or nearby non-target region) towards the identified relatively low-sensitivity region, monitoring the microbubble movement and/or cavitation, causing the ultrasound transducer to transmit sonications to the target region for commencing the ultrasound procedure (e.g., ablating the target tumor tissue), and/or monitoring the microbubble response during the ultrasound procedure, as described above.

In addition, the ultrasound controller 108, the MR controller 148 and/or the controller associated with the administration system controller 126 may include one or more modules implemented in hardware, software, or a combination of both. For embodiments in which the functions are provided as one or more software programs, the programs may be written in any of a number of high level languages such as PYTHON, FORTRAN, PASCAL, JAVA, C, C++, C#, BASIC, various scripting languages, and/or HTML. Additionally, the software can be implemented in an assembly language directed to the microprocessor resident on a target computer; for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for regulating microbubbles in a treatment procedure for a target region, the system comprising:
    an ultrasound transducer; and
    a controller configured to:
        (a) generate a tissue-sensitivity map including a plurality of regions, at least one of the regions being outside the target region, the tissue-sensitivity map assigning, to each of the regions, a sensitivity level indicative of tissue sensitivity to an interaction between the microbubbles and an acoustic beam;
        (b) select at least one interaction region based at least in part on the tissue-sensitivity map; and
        (c) activate the ultrasound transducer so as to generate the acoustic beam for interacting with the microbubbles in the selected at least one interaction region in the tissue-sensitivity map, thereby indirectly changing a characteristic of the microbubbles at the target region.

2. The system of claim 1, wherein the controller is further configured to determine at least one parameter associated with the ultrasound transducer based at least in part on the selected at least one interaction region in the tissue-sensitivity map.

3. The system of claim 2, wherein the controller is further configured to activate the ultrasound transducer based at least in part on the determined parameter associated with the ultrasound transducer.

4. The system of claim 1, wherein the treatment procedure involves utilization of the microbubbles, the system further comprises means for providing microbubbles to the target region for initializing the treatment procedure.

5. The system of claim 4, wherein the means for providing the microbubbles comprises an administration system for administering the microbubbles to the target region.

6. The system of claim 4, wherein the means for providing the microbubbles causes the ultrasound transducer to transmit ultrasound pulses to the target region to generate the microbubbles.

7. The system of claim 4, wherein the controller is further configured to perform step (c) only after a focusing property of the acoustic beam at the target region is optimized.

8. The system of claim 1, further comprising means for detecting the characteristic of the microbubbles in at least one of the target region, one of the regions in the tissue-sensitivity map, or a dedicated monitored region.

9. The system of claim 8, wherein the means for detecting the microbubble characteristic comprises the ultrasound transducer, an acoustic-signal detection device or a second ultrasound transducer.

10. The system of claim 8, wherein the controller is further configured to determine at least one parameter associated with the ultrasound transducer based at least in part on the detected microbubble characteristic.

11. The system of claim 1, wherein the generated acoustic beam causes cavitation of at least some of the microbubbles in the selected at least one interaction region.

12. The system of claim 11, wherein the controller is further configured to determine at least one parameter associated with the ultrasound transducer so as to select the at least some of the microbubbles for cavitation.

13. The system of claim 12, wherein the at least one parameter associated with the ultrasound transducer comprises at least one of a frequency, an amplitude or a phase associated with at least one transducer element of the ultrasound transducer.

14. The system of claim 1, wherein the tissue sensitivity comprises at least one of thermal sensitivity or sensitivity to microbubble cavitation.

15. The system of claim 1, wherein the microbubble characteristic comprises at least one of an amount, a concentration, a size distribution or a response of the microbubbles to the acoustic beam.

16. The system of claim 1, further comprising an imaging device for acquiring digital representations comprising a plurality of voxels of at least a portion of the regions in the tissue-sensitivity map, the controller being further configured to generate the tissue-sensitivity map based at least in part on the digital representations.

17. The system of claim 16, wherein the controller is further configured to determine an anatomical characteristic of the at least a portion of the regions in the tissue-sensitivity map based on the digital representations, the tissue-sensitivity map being generated based at least in part on the anatomical characteristic.

18. The system of claim 17, wherein the anatomical characteristic comprises at least one of a tissue type, a location, a size, or a function.

19. The system of claim 17, wherein the controller is further configured to generate the tissue-sensitivity map by assigning a sensitivity score to voxels of the at least a portion of the regions in the tissue-sensitivity map based at least in part on the anatomical characteristic associated therewith, the sensitivity score indicating a sensitivity level of the voxel to the interaction of the acoustic beam with the microbubbles.

20. The system of claim 19, wherein the selected at least one interaction region in the tissue-sensitivity map has a relatively low lower sensitivity score than the other ones of the regions in the tissue-sensitivity map.

21. The system of claim 19, wherein the controller is further configured to adjust at least one parameter associated with the ultrasound transducer based at least in part on the sensitivity scores assigned to the regions in the tissue-sensitivity map.

22. The system of claim 1, wherein the controller is further configured to adjust at least one parameter associated with the ultrasound transducer to cause at least some of the microbubbles to move from the target region to the selected at least one interaction region in the tissue-sensitivity map.

23. A method of regulating microbubbles in a treatment procedure for a target region, the method comprising:
at a controller operatively coupled to an ultrasound transducer:
(a) generating a tissue-sensitivity map including a plurality of regions, at least one of the regions being outside the target region, the tissue-sensitivity map assigning, to each of the regions, a sensitivity level indicative of tissue sensitivity to an interaction between the microbubbles and an acoustic beam;
(b) selecting at least one interaction region based at least in part on the tissue- sensitivity map; and
(c) activating the ultrasound transducer so as to generate the acoustic beam for interacting with the microbubbles in the selected at least one interaction region in the tissue-sensitivity map, thereby indirectly changing a characteristic of the microbubbles at the target region.

24. The method of claim 23, further comprising:
at the controller:
determining at least one parameter associated with the ultrasound transducer based at least in part on the selected at least one interaction region in the tissue-sensitivity map; and
activating the ultrasound transducer based at least in part on the determined parameter associated with the ultrasound transducer.

25. The method of claim 23, wherein:
the treatment procedure involves utilization of the microbubbles, and the method further comprises providing microbubbles to the target region for initializing the treatment procedure, including causing the ultrasound transducer to transmit ultrasound pulses to the target region to generate the microbubbles; and
the method includes perform step (c) only after a focusing property of the acoustic beam at the target region is optimized.

26. The method of claim 23, further comprising:
detecting the characteristic of the microbubbles in at least one of the target region, one of the regions in the tissue-sensitivity map, or a dedicated monitored region; and determining, at the controller, at least one parameter associated with the ultrasound transducer based at least in part on the detected microbubble characteristic.

27. The method of claim 23, wherein:
generating the acoustic beam causes cavitation of at least some of the microbubbles in the selected at least one interaction region; and
the method further comprises determining at the controller, at least one parameter associated with the ultrasound transducer so as to select the at least some of the microbubbles for cavitation;
wherein the at least one parameter associated with the ultrasound transducer comprises at least one of a frequency, an amplitude or a phase associated with at least one transducer element of the ultrasound transducer.

28. The method of claim 23, wherein:
the tissue sensitivity comprises at least one of thermal sensitivity or sensitivity to microbubble cavitation; and
the microbubble characteristic comprises at least one of an amount, a concentration, a size distribution or a response of the microbubbles to the acoustic beam.

29. The method of claim 23, further comprising:
acquiring digital representations comprising a plurality of voxels of at least a portion of the regions in the tissue-sensitivity map;
generating, at the controller, the tissue-sensitivity map based at least in part on the digital representations; and
determining, at the controller, an anatomical characteristic of the at least a portion of the regions in the tissue-sensitivity map based on the digital representations, the tissue-sensitivity map being generated based at least in part on the anatomical characteristic.

30. The method of claim 29, wherein:
the anatomical characteristic comprises at least one of a tissue type, a location, a size, or a function; and
the method further comprises generating, at the controller, the tissue-sensitivity map by assigning a sensitivity score to voxels of the at least a portion of the regions in the tissue-sensitivity map based at least in part on the anatomical characteristic associated therewith, the sensitivity score indicating a sensitivity level of the voxel to the interaction of the acoustic beam with the microbubbles.

31. The method of claim 30, wherein:
the selected at least one interaction region in the tissue-sensitivity map has a lower sensitivity score than the other ones of the regions in the tissue-sensitivity map; and
the method further comprises adjusting, at the controller, at least one parameter associated with the ultrasound transducer based at least in part on the sensitivity scores assigned to the regions in the tissue-sensitivity map.

32. The method of claim 23, further comprising adjusting, at the controller, at least one parameter associated with the ultrasound transducer to cause at least some of the microbubbles to move from the target region to the selected at least one interaction region in the tissue-sensitivity map.

* * * * *